United States Patent [19]

LeMahieu

[11] Patent Number: 4,616,091

[45] Date of Patent: Oct. 7, 1986

[54] NAPHTHALENYLOXY CARBOXYLIC ACIDS

[75] Inventor: Ronald A. LeMahieu, North Caldwell, N.J.

[73] Assignee: Hoffmann-La Roche Inc., Nutley, N.J.

[21] Appl. No.: 817,791

[22] Filed: Jan. 8, 1986

Related U.S. Application Data

[62] Division of Ser. No. 763,120, Aug. 7, 1985, abandoned, which is a division of Ser. No. 477,100, Mar. 21, 1983, Pat. No. 4,550,190.

[51] Int. Cl.$^4$ .............................................. C07C 69/76
[52] U.S. Cl. ...................................... 560/53; 562/462
[58] Field of Search .......................... 560/53; 562/462

[56] References Cited

U.S. PATENT DOCUMENTS 4,002,630  1/1977  Papenfuhs et al. ................. 562/462

FOREIGN PATENT DOCUMENTS 61800  10/1982  European Pat. Off. .

OTHER PUBLICATIONS

Kariakose, A. P. et al., J. Indian Chem. Soc., 49(11) 1197-8, 1972.

Primary Examiner—Paul J. Killos
Attorney, Agent, or Firm—Jon S. Saxe; Bernard S. Leon; Matthew Boxer

[57] ABSTRACT

Naphthalenyloxy carboxylic acids of the formula

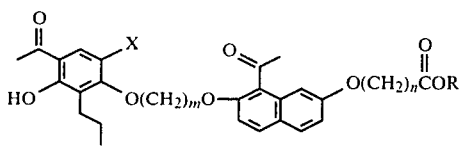

wherein X, R, m and n are as hereinafter set forth, are described. The compounds of formula I are antagonists of slow reacting substance of anaphylaxis (SRS-A), which renders them useful as agents for the treatment of allergic conditions.

7 Claims, No Drawings

NAPHTHALENYLOXY CARBOXYLIC ACIDS

This is a division of application Ser. No. 763,120, filed 8/7/85, abandoned which is a division of application Ser. No. 477,100 filed 3/21/83, now U.S. Pat. No. 4,550,190.

BRIEF SUMMARY OF THE INVENTION

The invention relates to compounds of the formula

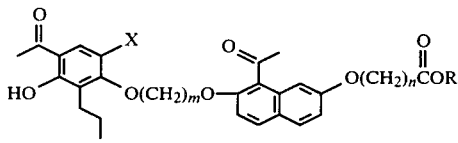

I wherein R is hydrogen or lower alkyl, X is hydrogen or halogen, m is an integer from 3 to 7, and n is an integer from 1 to 5, or, when R is hydrogen, salts thereof with pharmaceutically acceptable bases. The compounds of formula I are useful as agents for the treatment of allergic conditions.

In another aspect, the invention relates to intermediates of the formulas

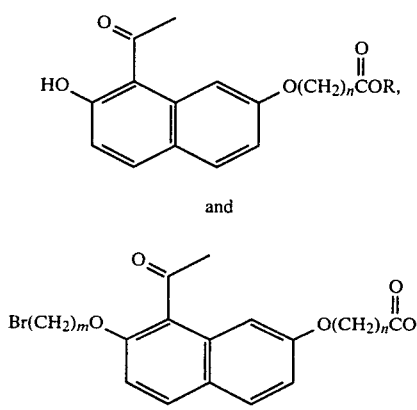

VII and

VIII wherein R, m and n are as previously described.

DETAILED DESCRIPTION OF THE INVENTION

As used herein, the term "lower alkyl" denotes a straight or branched chain saturated hydrocarbon containing 1 to 7 carbon atoms, for example, methyl, ethyl, propyl, isopropyl, butyl, t-butyl, neopentyl, pentyl, heptyl and the like. The term "halogen" denotes all the halogens, that is, bromine, chlorine, fluorine and iodine.

The invention relates to compounds of the formula

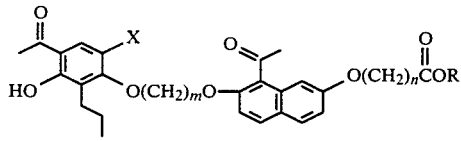

I wherein R is hydrogen or lower alkyl, X is hydrogen or halogen, m is an integer from 3 to 7, and n is an integer from 1 to 5, and, when R is hydrogen, salts thereof with pharmaceutically acceptable bases, which can be prepared as hereinafter described.

Preferred compounds of formula I are those wherein R and X are hydrogen. A most preferred compound of formula I is:

[[8-acetyl-7-[3-(4-acetyl-3-hydroxy-2-propylphenoxy)propoxy]-2-naphthalenyl]oxy]acetic acid Exemplary of the compounds of formula I are:

[[8-acetyl-7-[5-(4-acetyl-3-hydroxy-2-propylphenoxy)pentyloxy]-2-naphthalenyl]oxy]acetic acid

[[8-acetyl-7-[4-(4-acetyl-3-hydroxy-2-propylphenoxy)butoxy]-2-naphthalenyl]oxy]acetic acid

[[8-acetyl-7-[7-(4-acetyl-3-hydroxy-2-propylphenoxy)heptyloxy]-2-naphthalenyl]oxy]acetic acid 4-[[8-acetyl-7-[5-(4-acetyl-3-hydroxy-2-propylphenoxy)pentyloxy]-2-naphthalenyl]oxy]butanoic acid The compounds of formula I can be prepared according to Reaction Scheme I which follows:

Scheme I

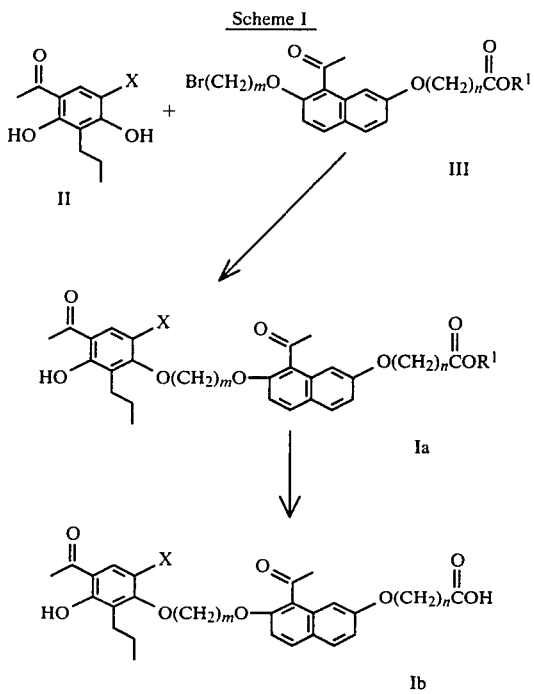

wherein X, m and n are as previously described, and $R^1$ is lower alkyl.

In Reaction Scheme I, the reaction of a compound of formula II with a compound of formula III to yield a compound of formula Ia is carried out under anhydrous conditions in an inert solvent, for example, acetone, methylethyl ketone, diethyl ketone, dimethylformamide or the like, at the reflux temperature of the reaction mixture, in dimethylformamide, preferably at a temperature in the range of 70°–100° C., and in the presence of an acid acceptor, for example, potassium carbonate or the like. The preferred solvent is a mixture of acetone and dimethylformamide. The resulting compound of formula Ia can be recovered utilizing conventional methods, for example, crystallization, chromatography or the like.

A resulting compound of formula Ia can be converted to a compound of formula Ib by hydrolysis which is carried out with an alkali metal hydroxide, for example, sodium hydroxide, potassium hydroxide or the like, in a mixture of water and a water miscible alcohol, for example, methanol, ethanol or the like, at a temperature in the range of from about room temperature to the reflux temperature. The resulting compound of formula Ib can be recovered utilizing conventional methods, for example, crystallization, chromatography or the like.

The starting materials for the preparation of the compounds of formula I can be prepared according to Reaction Scheme II which follows:

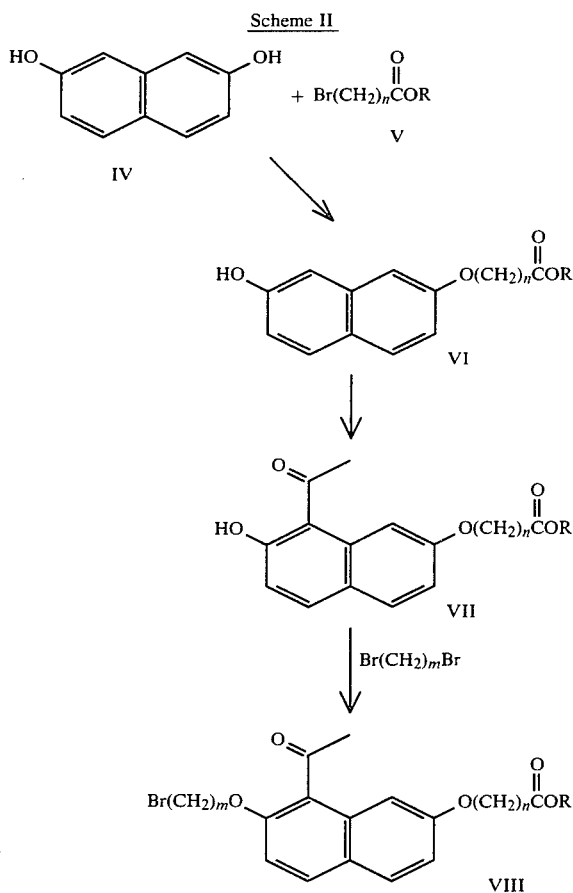

In Reaction Scheme II the reaction of a compound of formula IV with a compound of the formula V to yield a compound of formula VI is carried out from room temperature to reflux of the reaction mixture in an inert solvent, for example, acetone, methylethyl ketone, diethyl ketone or the like, in the presence of an acid acceptor, for example, potassium carbonate, sodium carbonate or the like. This reaction can also be carried out utilizing a base, for example, sodium hydride or the like, under anhydrous conditions in a solvent, for example, dimethylformamide, tetrahydrofuran, dioxane or the like, at a temperature in the range of from about 25° C. to about 70° C. The resulting compound of formula VI can be recovered utilizing conventional methods, for example, crystallization, chromatography or the like.

The conversion of a compound of formula VI to a compound of formula VII is conveniently carried out by reacting a compound of formula VI, in an inert solvent such as dichloroethane or nitromethane, with an acyl halide such as acetyl chloride and a Lewis acid such as aluminum chloride in the range of about 25° to the reflux temperature of the solvent. The resulting compound of formula VII can be recovered utilizing conventional methods, for example, crystallization, chromatography or the like.

The conversion of a compound of formula VII to a compound of formula VIII is conveniently carried out by reacting a compound of formula VII with a dihaloalkane such as 1,3-dibromopropane in the presence of potassium carbonate, sodium carbonate or the like, and in a solvent such as acetone, methylethyl ketone or the like. This reaction can also be carried out using a base such as sodium hydride, or the like, under anhydrous conditions in a solvent, for example, dimethylformamide, tetrahydrofuran, dioxane or the like, at a temperature in the range of from about 25° to about 70°. The resulting compound of formula VIII can be recovered utilizing conventional methods, for example, chromatography or the like.

Exemplary of intermediates of formula VII are:
3-[(8-Acetyl-7-hydroxy-2-naphthalenyl)oxy]propionic acid methyl ester;
6-[(8-Acetyl-7-hydroxy-2-naphthalenyl)oxy]hexanoic acid methyl ester; and the like.

Exemplary of the compounds of formula VIII are:
4-[[8-Acetyl-7-(5-bromopentyloxy)-2-naphthalenyl]oxy]butanoic acid methyl ester;
6-[[8-Acetyl-7-(5-bromopentyloxy)-2-naphthalenyl]oxy]hexanoic acid methyl ester;
[[8-Acetyl-7-(7-bromoheptyloxy)-2-naphthalenyl]oxy]acetic acid methyl ester; and the like.

This invention also relates to the pharmaceutically acceptable salts of the naphthalenyloxy carboxylic acid derivatives of formula I, wherein $R_4$ is hydrogen. Said salts can be prepared by reacting an acid of formula I with a base having a non-toxic, pharmacologically and pharmaceutically acceptable cation. In general, any base which will form a salt with a carboxylic acid and whose pharmacological properties will not cause an adverse physiological effect when ingested by a warmed blooded animal is considered as being within the scope of this invention. Suitable bases thus include, for example, the alkali metal and alkaline earth metal hydroxides, carbonates, for example, sodium hydroxide, potassium hydroxide, calcium hydroxide, potassium carbonate and the like, ammonia, primary, secondary and tertiary amines, such as monoalkylamines, dialkylamines, trialkylamines, nitrogen containing heterocyclic amines, for example, piperidine, amino acids such as lysine, and the like. The pharmaceutically acceptable salts thus produced are the functional equivalent of the corresponding phenoxycarboxylic acids of formula I and one skilled in the art will appreciate that, to the extent that the salts of the invention are useful in therapy, the variety of salts encompassed by this invention are limited only by the criterion that the bases employed in forming the salts be both non-toxic and physiologically acceptable.

The compounds of formula I of the invention are useful in the treatment of disorders in which slow reacting substance of anaphylaxis (SRS-A) is a mediator. The compounds of formula I are therefore useful in the treatment of allergic disorders which include skin afflictions, hay fever, chronic bronchitis, obstructive airways diseases such as asthma, allergic conditions of the eye, and allergic conditions of the gastro-intestinal tract, such as food allergies.

The useful antiallergic activity of the compounds of formula I is demonstrated in vitro and in warm-blooded animals utilizing standard procedures. Exemplary of such procedures are:

(a) Guinea Pig Ileum, In Vitro:

The guinea pig ileum bioassay system has been described by Orange and Austen, Adv. Immunol. 10: 105-144 (1969). A 1.5 cm segment is removed from animals weighing 300-400 g and suspended in an organ bath containing 10 ml of Tyrodes solution with $10^{-6}$M atropine sulfate and $10^{-6}$M pyrilamine maleate. The bath is maintained at 37° C. and aerated with a mixture of 95% oxygen and 5% carbon dioxide. The SRS-A utilized in this screen is obtained by challenging chopped lung fragments from actively sensitized guinea pigs with egg albumin, in vitro. A dose-response curve to SRS-A challenge is established for the ileum. The dose of SRS-A which gives 50% of the maximal contraction ($EC_{50}$) is then used for subsequent challenge. The drug concentration which inhibits, by 50%, the SRS-A-induced constriction of the guinea pig ileum is determined. In this bioassay system the standard SRS-A antagonist, 7-[3-(4-acetyl-3-hydroxy-2-propylphenoxy)-2-hydroxypropoxy]-4-oxo-8-propyl-4H-1-benzopyran-2-carboxylic acid, has an $IC_{50}$ of $3.5 \times 10^{-8}$M.

(b) Guinea Pig Bronchoconstriction, in Vivo:

Male guinea pigs (Hartley strain) weighing 300 to 450 grams are anesthetized with urethane (2 g/kg) intraperitoneally and a polyethylene cannula is inserted into the jugular vein for intravenous drug administration. Tracheal pressure is recorded from a cannula inserted in the trachea and connected to a Statham pressure transducer. Respiration is paralyzed with succinyl choline (1.2 mg/kg, i.v.) and the animals are mechanically respirated (Howard rodent respirator) at 40 breaths/minute and 2.5 cc tidal volume. Two minutes thereafter, propranolol (0.1 mg/kg, i.v.) is administered. Five minutes later, the animals are pretreated intravenously for 30 seconds (at 10 mg/kg) with test drug or control vehicle. The animals are subsequently challenged with a maximally constrictory dose of leukotriene $E_4$ also administered intravenously. The change (cm $H_2O$) between pre and peak ventilatory pressure readings is averaged for three control animals and five drug treated animals. The percent inhibition is calculated from the following formula:

$$\frac{\text{Control} - \text{Drug Treated}}{\text{control}} \times 100.$$

For determination of oral activity, spontaneously breathing animals are pretreated orally for 2 hours (at 100 mg/kg) prior to challenge with leukotriene $E_4$. 7-[3-(4-Acetyl-3-hydroxy-2-propylphenoxy)-2-hydroxypropoxy]-4-oxo-8-propyl-4H-1-benzopyran-2-carboxylic acid elicits a 98% inhibition at 10 mg/kg, i.v., but is orally inactive in this test.

(c) Guinea Pig Bronchoconstriction, In Vivo (Aerosol):

Male guinea pigs (Hartley strain) weighing 300 to 500 g are anesthetized with urethane (2 g/kg) intraperitoneally and a polyethylene cannula is inserted into the jugular vein for drug administration. Tracheal pressure is recorded from a cannula inserted in the trachea and connected to a Statham pressure transducer. After surgical preparation of the animals, a period of time is allowed for pulmonary functions to stabilize. The test compound is administered according to the following protocol. Propranolol (0.1 mg/kg) is administered intravenously while the animals breathed spontaneously. Five minutes thereafter, the animals are exposed for a five minute period to a 1% (w/v) aerosol solution of test compound (adjusted to an alkaline pH where necessary for drug solubilization) or to distilled water of the appropriate pH (for control purposes). A Monaghan (Model 750) ultrasonic nebulizer is used to administer all test compounds by inhalation. The nebulizer ultrasonic frequency is adjusted to produce particles in the 1-8$\mu$ diameter range (average 3$\mu$). Aqueous solutions are prepared fresh and introduced into the chamber of the nebulizer. The output of the nebulizer is made available to the animal by directing a bias flow of aerosol through a y tube connected to the tracheal cannula. At the end of the exposure period, the animals are paralyzed with succinylcholine (1.2 mg/kg, i.v.) and mechanically respirated (Harvard rodent respirator) at 40 breaths/minute and 2.5 cc tidal volume. Animals are then challenged with a maximum constrictory dose of leukotriene $E_4$ delivered intravenously 30 seconds after administration of the succinylcholine.

The change (cm $H_2O$) between pre and peak ventilatory pressure readings is averaged for three control animals and five drug treated animals. The percent inhibition is calculated from the following formula:

$$\frac{\text{Control} - \text{Drug Treated}}{\text{control}} \times 100$$

When various drug concentrations are tested, the percent inhibition at each concentration is plotted as log concentration (abscissa) versus percent inhibition (ordinate) and the $IC_{50}$ is determined from linear regression analysis.

In order to determine the duration of action (doa), the animals are prepared as described above, except that the time between aerosol exposure and challenge with $LTE_4$ is varied. All compounds are administered at a concentration of 1%. Duration of action is calculated from plots of time (abscissa) versus % inhibition (ordinate). The duration of action is defined as the time for the % inhibition to fall below 40%.

When the compounds of formula I, listed hereinafter in Table I, were utilized in the test procedures described above, the results set out in Table I were obtained:

TABLE I

| Test Compound | Guinea Pig Ileum In Vitro (M) $IC_{50}$ | Guinea Pig Bronchoconstriction, In Vivo % I 10 mg/kg I.V. | Guinea Pig Bronchoconstriction, In Vivo Aerosol $IC_{50}$ (%) | Aerosol Duration of Action (min.) |
|---|---|---|---|---|
| [[8-Acetyl-7-[3(4-acetyl-3-hydroxy-2-propylphenoxy)propoxy]-2-naphthalenyl]oxy] acetic acid | $2 \times 10^{-7}$ | $90 \pm 3$ | $0.014^a$ | 25 |
| [[8-Acetyl-7-[5-(4-acetyl-3-hydroxy-2-propylphenoxy) pentyloxy]-2-naphthalenyl]oxy] acetic acid | $2 \times 10^{-7}$ | $60 \pm 3$ | $0.14^a$ | |
| [[8-Acetyl-7-[3-(4-acetyl-6-chloro-3-hydroxy-2-propylphenoxy)propoxy]- | $5 \times 10^{-7}$ | $48 \pm 1$ | $0.14^a$ | |

TABLE I-continued

| Test Compound | Guinea Pig Ileum In Vitro (M) IC$_{50}$ | Guinea Pig Bronchoconstriction, In Vivo % I 10 mg/kg I.V. | Guinea Pig Bronchoconstriction, In Vivo Aerosol IC$_{50}$ (%) | Aerosol Duration of Action (min.) |
|---|---|---|---|---|
| 2-naphthalenyl]oxy] acetic acid | | | | |

$^a$IC$_{50}$ was determined using % inhibition values obtained 30 seconds after exposure to test drug.

A compound of formula I or a salt thereof when R$_4$ is hydrogen, or a composition containing a therapeutically effective amount of a compound of formula I or a salt thereof, when R$_4$ is hydrogen, can be administered by methods well known in the art. Thus, a compound of formula I, or a salt thereof when R$_4$ is hydrogen, can be administered either singly or with other pharmaceutical agents, for example, antihistamines, mediator release inhibitors, methyl xanthines, B$_2$ agonists or antiasthmatic sterioids such as prednisone and prednisolone, orally, parenterally, rectally or by inhalation, for example, in the form of an aerosol, micropulverized powder or nebulized solution. For oral administration they can be administered in the form of tablets, capsules, for example, in admixture with talc, starch, milk sugar or other inert ingredients, that is, pharmaceutically acceptable carriers, or in the form of aqueous solutions, suspensions, elixirs or aqueous alcoholic solutions, for example, in admixture with sugar or other sweetening agents, flavoring agents, colorants, thickeners and other conventional pharmaceutical excipients. For parenteral administration, they can be administered in solutions or suspension, for example, as an aqueous or peanut oil solution or suspension using excipients and carriers conventional for this mode of administration. For administration as aerosols, they can be dissolved in a suitable pharmaceutically acceptable solvent, for example, ethyl alcohol or combinations of miscible solvents, and mixed with a pharmaceutically acceptable propellant. Such aerosol compositions are packaged for use in a pressurized container fitted with an aerosol valve suitable for release of the pressurized composition. Preferably, the aerosol valve is a metered valve, that is one which on activation releases a predetermined effective dose of the aerosol composition.

In the practice of the invention, the dose of a compound of formula I or a salt thereof when R$_4$ is hydrogen to be administered and the frequency of administration will be dependent on the potency and duration of activity of the particular compound of formula I or salt to be administered and on the route of administration, as well as the severity of the condition, age of the mammal to be treated and the like. Doses of a compound of formula I or a salt thereof when R$_4$ is hydrogen contemplated for use in practicing the invention are in the range of from about 25 to about 1000 mg per day, preferably about 25 to about 250 mg either as a single dose or in divided doses.

The Examples which follow further illustrate the invention. All temperatures are in degrees centigrade, unless other wise stated.

EXAMPLE I

Preparation of [(7-Hydroxy-2-napththalenyl)oxy] acetic acid methyl ester. A mixture of 32 g of 2,7-dihydroxynaphthalene and 36 g of anhydrous potassium carbonate in 250 ml of anhydrous acetone was stirred at 22° for 2 hours and 40 minutes. Methyl bromoacetate (20.8 ml) was added and stirring at room temperature was continued for 19 hours. The reaction mixture was filtered and the solid was washed well with acetone. The filtrate was concentrated in vacuo and the residue was acidified and extracted with methylene chloride. The methylene chloride extract was washed with 1N sodium hydroxide (3×200 ml). The combined aqueous extract was left at room temperature for 16 hours and then acidified and extracted with ethyl acetate. The extract was washed with saturated sodium bicarbonate solution. The insoluble sodium salt which formed was filtered, combined with the aqueous layer and acidified. The product was extracted with ethyl acetate and the dried (over magnesium sulfate) extract was concentrated in vacuo to a solid (17 g). This was esterified by refluxing in 300 ml of methanol containing 4 ml of concentrated sulfuric acid for 5.5 hours. The solvent was removed in vacuo and the residue was taken up in methylene chloride and washed with sodium bicarbonate solution. The methylene chloride was removed in vacuo and the residue was crystallized from methylene chloride-hexane to give 12.8 g, mp 122°–123°, of [(7-Hydroxy-2-naphthalenyl)oxy]acetic acid methyl ester. An additional 2.3 g was obtained by chromatography of the filtrate on 200 g of silica gel using 10% ethyl acetate-toluene. The total yield was 33%.

EXAMPLE 2

Preparation of [(8-Acetyl-7-hydroxy-2-naphthalenyl)oxy]acetic acid methyl ester. To a mixture of 5.8 g of aluminum chloride in 100 ml of dichlorethane was added 3.1 ml of acetyl chloride followed by 8.0938 g of [(7-hydroxy-2-naphthalenyl)oxy]acetic acid methyl ester. The mixture was stirred at room temperature for 2 hours and then at reflux for 19 hours. The reaction mixture was cooled, 100 ml of 6N hydrochloric acid was added and, after shaking well, the product was extracted with methylene chloride. The extract was washed with sodium bicarbonate solution, dried over magnesium sulfate and concentrated in vacuo to a solid which was recrystallized from methylene chloride-ether to give 6.030 g (63% yield), mp 113°–114°, of [(8-Acetyl-7-hydroxy-2-naphthalenyl)oxy]acetic acid methyl ester. An additional 0.878 g of product was obtained on concentration of the filtrate to a smaller volume.

EXAMPLE 3

Preparation of [[8-Acetyl-7-(3-bromopropoxy)-2-naphthalenyl]oxy]acetic acid methyl ester. A mixture of 4.989 g of [(8-acetyl-7-hydroxy-2-naphthalenyl)oxy]acetic acid methyl ester, 18 ml of 1,3-dibromopropane and 3.7 g of anhydrous potassium carbonate in 150 ml of anhydrous acetone was stirred at reflux for 16.5 hours. The reaction mixture was filtered and the filtrate was concentrated in vacuo. The residue was chromatographed on 250 g of silica gel. Elution with 10% ethyl acetate-toluene gave 6.730 g (95% yield) of [[8-acetyl-7-

(3-bromopropoxy)-2-napththalenyl]oxy]acetic acid methyl ester as an oil.

EXAMPLE 4

Preparation of [[8-Acetyl-7-[3-(4-acetyl-3-hydroxy-2-propylphenoxy)propoxy]-2-naphthalenyl]oxy]acetic acid methyl ester. A mixture of 1.7314 g of 1-(2,4-dihydroxy)-3-propylphenyl)ethanone, 3.5290 g of [[8-acetyl-7-(3-bromopropoxy)-2-naphthalenyl]oxy]acetic acid methyl ester and 1.90 g of anhydrous potassium carbonate in 75 ml of dry acetone was stirred at reflux for 30 hours. An additional 0.1938 g of 1-(2,4-dihydroxy-3-propylphenyl)ethanone and 1.0 g of potassium carbonate were added along with 10 ml anhydrous DMF and reflux was continued for 20 hours. The reaction mixture was filtered and the filtrate was concentrated in vacuo. The residue was treated with aqueous hydrochloric acid and extracted with ethyl acetate. The dried (over magnesium sulfate) extract was concentrated in vacuo and the solid residue was recrystallized from methanol-water to give 3.1737 g (70% yield), mp 104°–107°, of [[8-Acetyl-7-[3-(4-acetyl-3-hydroxy-2-propylphenoxy)-propoxy]-2-naphthalenyl]oxy]acetic acid methyl ester.

EXAMPLE 5

[[8-Acetyl-7-[3-(4-acetyl-3-hydroxy-2-propylphenoxy)propoxy]-2-naphthalenyl]oxy]acetic acid. A solution of 3.17 g of [[8-acetyl-7-[3-(4-acetyl-3-hydroxy-2-propylphenoxy)propoxy]-2-naphthalenyl]oxy]acetic acid methyl ester in 100 ml of methanol and 30 ml of 1.0N sodium hydroxide was stirred at reflux for 4 hours. The methanol was removed in vacuo and the pH of the residue was adjusted to 2.0. The product was extracted with ethyl acetate and the dried (over magnesium sulfate) extract was concentrated to a solid which was purified by HPLC using a solvent of acetic acid:ethyl acetate:toluene (5:20:75). Recrystallization of the combined pure fractions from ethyl acetate-hexane gave 2.48 g (81% yield), mp 140°–141°, of [[8-Acetyl-7-[3-(4-acetyl-3-hydroxy-2-propylphenoxy)propoxy]-2-naphthalenyl]oxy]acetic acid.

EXAMPLE 6

Preparation of [[8-Acetyl-7-(5-bromopentyloxy)-2-naphthalenyl]oxy]acetic acid methyl ester. A mixture of 1.1 g of [[8-acetyl-7-hydroxy-2-naphthalenyl]oxy]acetic acid methyl ester, 9.2 g of 1,5-dibromopentane and 0.83 g of anhydrous potassium carbonate in 30 ml of anhydrous acetone was stirred at reflux for 17 hours. The reaction mixture was filtered and filtrate was concentrated at 60° C./0.15 mm to an oil which was purified by flash column chromatography to yield 1.7 g of [[8-Acetyl-7-(5-bromopentyloxy)-2-naphthalenyl]oxy]acetic acid methyl ester as an oil.

EXAMPLE 7

Preparation of [[8-Acetyl-7-[5-(4-acetyl-3-hydroxy-2-propylphenoxy)-pentyloxy]-2-naphthalenyl]oxy]acetic acid methyl ester. A mixture of 1.66 g of [[8-Acetyl-7-(5-bromopentyloxy)-2-naphthalenyl]oxy]acetic acid methyl ester, 0.76 g of 1-[2,4-dihydroxy-3-propylphenoxy]ethanone and 0.81 g of anhydrous potassium carbonate in 30 ml of anhydrous acetone and 10 ml of anhydrous dimethylformamide was stirred at reflux. An additional 0.8 g of anhydrous potassium carbonate was added after 15 hours. Reflux was continued for a total of 22 hours. The reaction mixture was filtered and the filtrate was concentrated in vacuo to an oil which was treated with ether and water. The organic phase was separated and washed with 1N sodium hydroxide, water and sodium chloride solution. The black oil from concentration of the organic phase was purified by flash column chromatography to yield 1.45 g. mp 87°–89° (69%) of [[8-Acetyl-7-[5-(4-acetyl-3-hydroxy-2-propylphenoxy)-pentyloxy]-2-napththalenyl]oxy]acetic acid methyl ester.

EXAMPLE 8

Preparation of [[8-Acetyl-7-[5(4-acetyl-3-hydroxy-2-propylphenoxy)pentyloxy]-2-naphthalenyl]oxy]acetic acid. To a suspension of 1.45 g of [[8-acetyl-7-[5-(4-acetyl-3-hydroxy-2-propylphenoxy)pentyloxy]-2-naphthalenyl]oxy]acetic acid methyl ester in 54 ml of methanol, was added 27 ml of 1N sodium hydroxide. The reaction mixture was stirred at reflux for one hour and 20 minutes. The methanol was removed in vacuo and the aqueous residue was acidified to pH3. The precipitate was dissolved in chloroform, dried (magnesium sulfate), and the solid obtained from the concentrated chloroform solution was recrystallized from ethylacetate-hexane to yield 1.1 g, mp 103°–106° C. (78%) of [[8-Acetyl-7-[5-(4-acetyl-3-hydroxy-2-propylphenoxy)-pentyloxy]-2-naphthalenyl]oxy]acetic acid.

EXAMPLE 9

Preparation of [[8-Acetyl-7-[3-(4-acetyl-6-chloro-3-hydroxy-2-propylphenoxy)propoxy]-2-naphthalenyl]oxy]acetic acid methyl ester. A mixture of 1.5 g of [[8-acetyl-7-(3-bromopropoxy)-2-naphthalenyl]oxy]acetic acid methyl ester, 0.87 g of 1-(5-chloro-2,4-dihydroxy-3-propylphenyl)-ethanone and 0.79 g of anhydrous potassium carbonate in 45 ml of anhydrous acetone was stirred at reflux. An additional 1 g of anhydrous potassium carbonate was added after 17 hours and 24 hours. Refluxing was continued for a total of 39 hours. The reaction mixture was filtered and filtrate was concentrated in vacuo to an oil which was purified by flash column chromatography to yield 2 g of oil. The oil was triturated with hexane and solid was filtered to give 1.3 g, mp 121°–124° (63%) of [[8-Acetyl-7-[3-(4-acetyl-6-chloro-3-hydroxy-2-propylphenoxy)propoxy]-2-naphthalenyl]oxy]acetic acid methyl ester.

EXAMPLE 10

Preparation of [[8-Acetyl-7-[3-(4-acetyl-6-chloro-3-hydroxy-2-propylphenoxy)propoxy]-2-naphthalenyl]oxy]acetic acid. A mixture of 1.3 g of [[8-acetyl-7-[3-(4-acetyl-6-chloro-3-hydroxy-2-propylphenoxy)propoxy]-2-naphthalenyl]oxy]acetic acid methyl ester, 48 ml of methanol and 24 ml of 1N sodium hyroxide was stirred at reflux for one hour and 20 minutes. The methanol was removed in vacuo the aqueous solution was acidified to pH 3. The sticky solid was extracted with chloroform, washed with water, dried over magnesium sulfate and concentrated in vacuo to give an oil which was crystallized from ether to yield 0.93 g (78%) of [[8-Acetyl-7-[3-(4-acetyl-6-chloro-3-hydroxy-2-propylphenoxy)propoxy]-2-naphthalenyl]oxy]acetic acid, mp 132°–134° C.

EXAMPLE 11

Preparation of 4-[(8-Acetyl-7-hydroxy-2-naphthalenyl)oxy]butanoic acid methyl ester. Under argon, 2.8 ml of acetyl chloride was added to a suspension of 5.15 g of aluminum chloride in 120 ml of dichloroethane. Then 8 g of 4-[(7-hydroxy-2-naphthalenyl)oxy]- butanoic acid methyl ester was added and the resulting mixture was stirred at room temperature for 30 minutes and at reflux for 16 hours. The solution was filtered and the dark residue was broken up with 3N hydrochloric acid and extracted with methylene chloride. The filtrate was combined with the methylene chloride extract, washed and dried to give a black oil which was purified by HPLC (eluting with 2% ethylacetate/toluene) to yield 2.72 g (29%) of 4-[(8-Acetyl-7-hydroxy-2-naphthalenyl)oxy]butanoic acid methyl ester as an oil.

EXAMPLE 12

Preparation of 4-[[8-Acetyl-7-(3-bromopropoxy)-2-naphthalenyl]oxy]butanoic acid methyl ester. A mixture of 2.7 g of 4[(8-acetyl-7-hydroxy-2-naphthalenyl)oxy]-butanoic acid methyl ester, 9.6 ml of dibromopropane and 1.95 g of anhydrous potassium carbonate in 100 ml of anhydrous acetone was stirred at reflux for 17 hours. The mixture was filtered and the filtrate was concentrated in vacuo to an oil which was purified by open column chromatography (eluting with 2.5%-10% of ethylacetate/toluene) to yield 2.98 g (75%) of 4-[[8-Acetyl-7-(3-bromopropoxy)-2-naphthalenyl]oxy]-butanoic acid methyl ester as an oil.

EXAMPLE 13

Preparation of 4-[[8-Acetyl-7-[3-(4-acetyl-3-hydroxy-2-propylphenoxy)propoxy]-2-naphthalenyl]oxy]-butanoic acid methyl ester. A mixture of 1.8 g of 4-[[8-acetyl-7-(3-bromopropoxy)-2-naphthlenyl]oxy]-butanoic acid methyl ester, 1 g of 1-(2,4-dihydroxy-3-propylphenyl)ethanone and 0.9 g of anhydrous potassium carbonate in 30 ml of anhydrous acetone and 6 ml of anhydrous dimethylformamide was stirred at reflux for 15 hours. The mixture was filtered and the filtrate was concentrated in vacuo to an oil which was dissolved in ethylacetate and washed with water, 1N sodium hydroxide solution and sodium chloride solution. The oil resulting from the ethyl acetate extract was purified by flash column chromotography to yield 1.44 g (63%) of 4-[[8-Acetyl-7-[3-(4-acetyl-3-hydroxy-2-propylphenoxy)propoxy]-2-naphthalenyl]oxy]butanoic acid methyl ester as an oil.

EXAMPLE 14

Preparation of 4-[[8-Acetyl-7-[3-(4-acetyl-3-hydroxy-2-propylphenoxy)propoxy]-2-naphthalenyl]oxy]-butanoic acid. A mixture of 1.44 g of 4-[[8-acetyl-7-[3-(4-acetyl-3-hydroxy-2-propylphenoxy)propoxy]-2-naphthalenyl]oxy]butanoic acid methyl ester and 27 ml of 1N sodium hydroxide in 54 ml of methanol was stirred at reflux for an hour. The methanol was removed in vacuo and the clear solution was acidified to pH 3. The precipitate was extracted with chloroform and dried. The resulting semi-solid was purified by flash column chromatography (eluting with 2% methanol/ethylacetate) to yield 0.9 g (64%) of 4-[[8-Acetyl-7-[3-(4-acetyl-3-hydroxypropylphenoxy)propoxy]-2-naphthalenyl]oxy]butanoic acid of mp 121°–124°.

EXAMPLE 15

| CAPSULE FORMULATION | | | | |
| --- | --- | --- | --- | --- |
| | mg/capsule | | | |
| Ingredients | 25 mg | 50 mg | 100 mg | 200 mg |
| [[8-acetyl-7-[3-(4-acetyl-3-hydroxy-2-propylphenoxy)propoxy]-2-naphthalenyl]oxy] acetic acid. | 25 | 50 | 100 | 200 |
| Lactose | 375 | 155 | 200 | 140 |
| Starch | 30 | 30 | 35 | 40 |
| Talc | 20 | 15 | 15 | 20 |
| Weight of capsule | 450 mg | 250 mg | 350 mg | 400 mg |

Procedure

Mill [[8-acetyl-7-[3-(4-acetyl-3-hydroxy-2-propylphenoxy)propoxy]-2-naphthalenyl]oxy]acetic acid, lactose and starch in a suitable mixer. Mill. Add talc and mix well. Encapsulate on suitable equipment.

EXAMPLE 16

| TABLET FORMULATION (Wet granulation) | | | | |
| --- | --- | --- | --- | --- |
| | mg/tablet | | | |
| Ingredients | 25 mg | 50 mg | 100 mg | 200 mg |
| [[8-acetyl-7-[3-(4-acetyl-3-hydroxy-2-propyl phenoxy)propoxy]-2-naphthalenyl] oxy acetic acid. | 25 | 50 | 100 | 200 |
| Lactose | 280 | 153 | 187 | 171 |
| Modified Starch | 55 | 25 | 35 | 45 |
| Pregelatinized Starch | 35 | 20 | 25 | 30 |
| Distilled water q.s. | — | — | — | — |
| Magnesium Stearate | 5 | 2 | 3 | 4 |
| Weight of tablet | 400 mg | 250 mg | 350 mg | 450 mg |

Procedure

Mix, [[8-acetyl-7-[3-(4-acetyl-3-hydroxy-2-propylphenoxypropoxy]-2-naphthalenyl]oxy]acetic acid, lactose, modified starch and pregelatinized starch in a suitable mixer. Granulate with sufficient distilled water to proper consistency. Mill. Dry in a suitable oven. Mill and mix with magnesium stearate for 3 minutes. Compress on a suitable press equipped with appropriate punches.

EXAMPLE 17

| TABLET FORMULATION (Direct Compression) | |
| --- | --- |
| Ingredients | mg/tablet 25 mg |
| [[8-acetyl-7-[3-(4-acetyl-3-hydroxy-2-propylphenoxy)propoxy]-2-naphthalenyl] oxy acetic acid. | 25 |
| Lactose | 181 |
| Avicel | 55 |
| Direct Compression Starch | 35 |
| Magnesium Stearate | 4 |
| Weight of tablet | 300 mg |

Procedure:

Mix [[8-acetyl-7-[3-(4-acetyl-3-hydroxy-2-propylphenoxy)propoxy]-2-naphthalenyl]oxy]acetic acid with an equal amount of lactose. Mix well. Mix with avicel and direct compression starch, and the remaining amount of lactose. Mix well. Add magnesium stearate and mix for 3 minutes. Compression on a suitable press equipped with appropriate punches.

I claim:

1. A compound of the formula

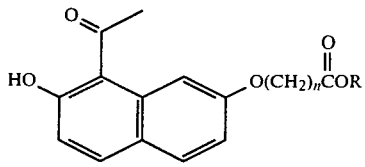

VII wherein R is hydrogen or lower alkyl, and n is an integer of 1 to 5.

2. A compound in accordance with claim 1, 4-[(8-Acetyl-7-hydroxy-2-naphthalenyl)oxy]butanoic acid methyl ester.

3. A compound in accordance with claim 1, [(8-Acetyl-7-hydroxy-2-naphthalenyl)oxy]acetic acid methyl ester.

4. A compound of the formula

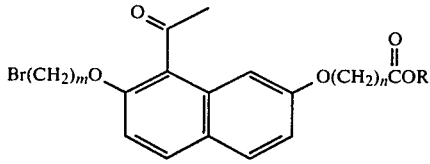

VIII wherein R is hydrogen or lower alkyl, m is an integer of 3 to 7, and n is an integer of 1 to 5.

5. A compound in accordance with claim 4, [[8-Acetyl-7-(3-bromopropoxy)-2-naphthalenyl]oxy]acetic acid methyl ester.

6. A compound in accordance with claim 4, [[8-acetyl-7-(5-bromopentyloxy)-2-naphthalenyl]oxy]acetic acid methyl ester.

7. A compound in accordance with claim 4, 4-[[8-acetyl-7-(3-bromopropoxy)-2-naphthalenyl]oxy]butanoic acid methyl ester.

* * * * *